United States Patent
Crawley et al.

(10) Patent No.: US 6,277,150 B1
(45) Date of Patent: Aug. 21, 2001

(54) FACIAL IMPLANT HAVING ONE POROUS SURFACE

(75) Inventors: Jerald M. Crawley; Stanislaw L. Zukowski, both of Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 09/330,549

(22) Filed: Jun. 11, 1999

(51) Int. Cl.[7] .................................................. A61F 2/28
(52) U.S. Cl. ........................................ 623/17.18; 623/23.74
(58) Field of Search ........................... 623/17.18, 15.12, 623/15.11, 17.19, 23.72, 23.76, 23.74, 8; 606/151

(56) References Cited

U.S. PATENT DOCUMENTS

| | | |
|---|---|---|
| 3,443,261 | 5/1969 | Battista et al. . |
| 3,992,725 | 11/1976 | Homsy . |
| 4,129,470 | 12/1978 | Homsy . |
| 4,344,191 | 8/1982 | Wagner . |
| 4,576,608 | 3/1986 | Homsy . |
| 4,790,849 | 12/1988 | Terino . |
| 4,863,974 | 9/1989 | Mallouk et al. . |
| 4,969,901 | 11/1990 | Binder . |
| 5,098,779 | 3/1992 | Kranzler et al. . |
| 5,133,754 | 7/1992 | Laghi . |
| 5,421,831 | 6/1995 | Giampapa . |
| 5,545,226 | 8/1996 | Wingo et al. . |
| 5,593,441 | * 1/1997 | Lichenstein et al. ............. 623/11.11 |
| 5,728,157 | * 3/1998 | Prescott ............................. 623/11.11 |
| 5,782,913 | 7/1998 | Schindler et al. . |
| 5,863,297 | 1/1999 | Walter et al. . |
| 5,876,447 | 3/1999 | Arnett . |
| 6,106,558 | * 8/2000 | Picha ................................. 623/23.74 |

FOREIGN PATENT DOCUMENTS 9522359   8/1995   (WO) .

OTHER PUBLICATIONS

Berman M et al. The Use of Gore–Tex® E–PTFE Bonded to Silicone Rubber As An Alloplastic Implant Material. Laryngoscope 1986; 96(5):480–483.

Lewis RP et al. Sheets, 3–D Strands, Trimensional (3–D) Shapes, and Sutures of Either Reinforced or Nonreinforced Expanded Polytetrafluoroethylene for Facial Soft–Tissue Suspension, Augmentation, and Reconstruction. Journal of Long–Term Effects of Medical Implants 1998;8(1):19–42.

* cited by examiner

Primary Examiner—Bruce Snow
(74) Attorney, Agent, or Firm—Wayne House

(57) ABSTRACT

A three dimensional facial space-filling implant adapted for filling space subcutaneously, said space being located primarily at the interface of a soft tissue surface and a bone surface. The article has a length, width and thickness wherein the thickness is oriented substantially orthogonal to first and second substantially opposing surfaces of the article. The thickness varies according to location along the length and width. The first surface is adapted to be substantially in contact with the soft tissue surface when implanted. This first surface is substantially porous having void spaces of size adequate to allow tissue ingrowth into at least a portion of the void spaces. The second surface is adapted to be substantially in contact with the bone surface when implanted and is substantially non-porous to substantially prevent ingrowth of bony tissue into the second surface. The first surface is preferably porous polytetrafluoroethylene and the thickness and second surface are preferably silicone.

8 Claims, 1 Drawing Sheet

FACIAL IMPLANT HAVING ONE POROUS SURFACE

FIELD OF THE INVENTION

The present invention relates to space-filling implants useful in plastic surgery and particularly to three dimensional facial implants having a solid-core (non-hollow) construction.

BACKGROUND OF THE INVENTION

Implantable articles of various shapes have been used for some time in plastic surgery to fill space subcutaneously in order to provide a more normal or desirable profile to the exterior surface of that portion of a person's body. These implants have traditionally been made primarily of elastomeric materials, particularly silicone. These types of articles are effective for their primary purpose of filling space in order to provide the desired exterior body contours, however, they have various disadvantages including a propensity to migrate from their site of original implantation if not properly anchored or attached. The typical silicone space-filling implant intended for facial repair is a solid article made from non-porous or substantially non-porous silicone. They are most commonly used when appropriately shaped for the repair of chins, cheeks and zygomatic arches. See, for example, U.S. Pat. No. 4,344,191 to Wagner and U.S. Pat. No. 4,790,849 to Terino.

In addition to facial implants, space-filling implants of many various designs are also used in other areas of the body. In particular, implants of various designs and constructions have long been used for breast augmentation. These devices are most typically constructed from silicone envelopes containing a soft filling material such as silicone gels. Implants of this type are of hollow-core construction and are beyond the scope of the present invention.

Materials other than elastomers have also been used for facial space-filling implants, most notably porous expanded polytetrafluoroethylene (ePTFE). Materials of this type are made as taught by U.S. Pat. Nos. 3,953,566 and 4,187,390 to Gore. ePTFE is commonly used as an implantable material because it is highly inert and thus typically provokes little if any adverse reaction when implanted. It is frequently used for tubular vascular grafts, sheet materials for patching membranes and blood vessels, dental barriers and sutures. It is also sold as a facial implant available from W. L. Gore and Associates, Inc. Flagstaff Aria., as GORE SUBCUTANEOUS AUGMENTATION MATERIAL™ (S.A.M.).

U.S. Pat. No. 5,098,779 to Kranzler et al. and PCT Published Application WO 95/22359 to Sharber et al. describe ePTFE space filling implants wherein the relatively soft ePTFE is rendered carvable (for shaping by a surgeon) by either coating or impregnating the porous ePTFE with a resorbable material, or by laminating it with alternating layers of another material such as silicone or fluorinated ethylene propylene (FEP) in order to render it adequately stiff for carving.

An article entitled "The Use of Gore-Tex® E-PTFE Bonded to Silicone Rubber as an Alloplastic Implant Material" (Berman et al., LARYNGOSCOPE, Vo. 96, No. 5, May 1986) describes the evaluation of implanted composite sheets of ePTFE sheet material laminated to sheets of silicone. Another article entitled "Sheets, 3-D Strands, Trimensional (3-D) Shapes, and Sutures of Either Reinforced or Nonreinforced Expanded Polytetrafluoroethylene for Facial Soft-Tissue Suspension, Augmentation, and Reconstruction" (Lewis et al., Journal of Long-Term Effects of Medical Implants, 8(1):19–42(1998)) describes facial repair implants of ePTFE having various shapes.

Facial space-filling implants of the types described above typically have exterior surfaces which are virtually entirely non-porous (e.g., silicone implants) or alternatively are virtually entirely porous (e.g., conventional ePTFE implants). The implants with porous exterior surfaces allow tissue ingrowth into those porous surfaces if they offer adequately large void spaces, typically of about 8–10 microns or larger, preferably larger than about 20 microns and less preferably of about 50 microns or larger. Tissue ingrowth results in a stable implant which is unlikely to have any tendency to migrate from its site of original implantation. Conversely, implants having substantially non-porous surfaces, that is either completely non-porous or having pores of too small of a size to accommodate any appreciable amount of tissue ingrowth, require suturing to adjacent body tissue for the necessary anchoring. Inadequate suturing frequently allows the implant to migrate away from its intended location.

While the ingrowth of soft tissue into an implant having porous exterior surfaces is desirable for stability of location, it is possible to dissect the attached soft tissue if it should become necesssary to remove the implant for any reason. However, if hard tissue (e.g., bone) has grown into the void spaces of the porous implant, the implant can be extremely difficult to dissect free should its removal be necessary.

SUMMARY OF THE INVENTION

The present invention relates to a three dimensional facial space-filling implant adapted for filling space subcutaneously, said space being located primarily at the interface of a soft tissue surface and a bone surface. The article has a length, width and thickness wherein the thickness is oriented substantially orthogonal to first and second substantially opposing surfaces of the article. The thickness varies according to location along the length and width. The first surface is adapted to be substantially in contact with the soft tissue surface when implanted, and is substantially porous having void spaces of size adequate to allow tissue ingrowth into at least a portion of the void spaces. The second surface is adapted to be substantially in contact with the bone surface when implanted and is substantially non-porous to substantially prevent ingrowth of bony tissue into the second surface.

The different porosity characteristics of the first and second surfaces allows for the ingrowth of soft tissue into the first surface to provide stability of implant location while substantially or entirely precluding ingrowth of hard tissue into the second surface which, if it occurred to a significant degree, would render the implant difficult to remove. Thus the characteristics of the implant of the present invention allow the implant to be relatively easily removed if necessary while still allowing ingrowth of soft tissue into the first surface for implant stability.

The thickness or core of the implant is preferably a solid or non-hollow core. The core material is preferably an elastomer and most preferably a silicone (polydimethyl siloxane). Other implantable elastomers may also be used for the core including polyurethanes and fluoroelastomers.

In a preferred embodiment, the present invention comprises a three dimensional implant such as a chin, cheek or nasal implant made from silicone (polydimethyl siloxane). The silicone shape is provided with a porous covering on one surface which is adapted to face toward and contact the soft tissue following implantation. The opposing surface remains as non-porous or substantially non-porous silicone. The porous covering is preferably porous polytetrafluoroethylene and more preferably porous expanded polytetrafluoroethylene (ePTFE), made as taught by U.S. Pat. Nos. 3,953,566 and 4,187,390, incorporated by reference herein. Other porous materials may also be used. For example, a solid core implant of, for example, silicone or polyurethane may be provided with one surface of a porous material of the same type. Various methods of making elastomeric materials porous are known in the art.

Typical chin, cheek and nasal implants are suitable three dimensional shapes which usually have two opposing exterior surfaces, with one surface commonly being concave and the opposite being convex. The convex surface is adapted for facing outwardly toward the patient's skin and accordingly is intended to be primarily or entirely in contact with overlying soft tissue. Conversely, the concave surface is adapted for facing toward and substantially or entirely being in contact with the underlying bone. In a preferred embodiment of the present invention, the convex surface is made to be adequately porous to accommodate soft tissue ingrowth while the opposing concave surface is made to be adequately non-porous to substantially prevent the ingrowth of hard tissue. More preferably, the convex surface is substantially or entirely ePTFE of adequate pore size to allow soft tissue ingrowth while the concave surface is substantially or entirely non-porous silicone.

This embodiment is most simply manufactured by affixing a sheet of ePTFE of suitable porosity to one surface of the silicone implant using a medical grade adhesive such as a suitable silicone adhesive. The edges of the ePTFE sheet may be trimmed as desired after curing of the ePTFE adhesive. Alternatively, the ePTFE sheet may be fitted into one side of a mold cavity used to form the silicone shape prior to filling the cavity with uncured silicone. It may be desirable to wet the surface of the ePTFE sheet with a suitable solvent to better enable the uncured silicone to interpenetrate the void spaces of that surface of the ePTFE sheet.

DETAILED DESCRIPTION OF THE DRAWINGS

Figure 1:
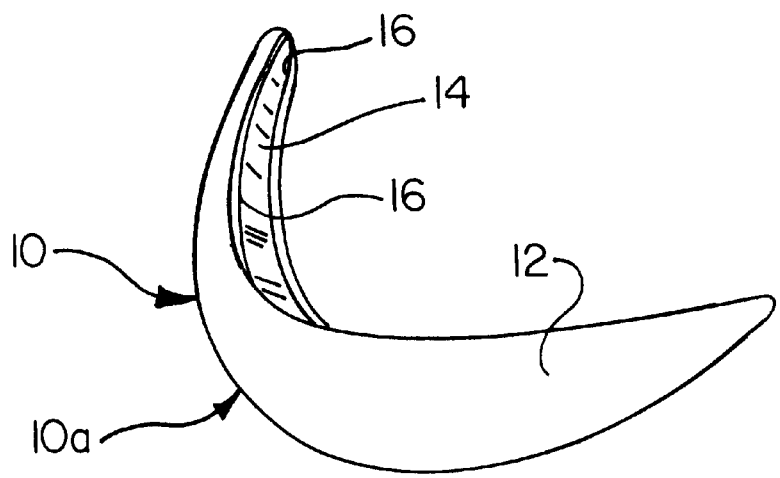
FIG. 1 is a perspective view of a typically shaped facial implant for chin repairs, made according to the present invention.

FIG. 1 shows a perspective view of a facial implant 10 of the present invention suitably shaped for a typical chin augmentation. The chin implant 10a has a convex exterior surface 12 adapted for facing outwardly toward the overlying skin following implantation.

Exterior surface 12 is provided with porosity of adequate pore size in order to accommodate soft tissue ingrowth. Implant 10a also has a concave interior surface 14 which opposes the exterior surface 12. This interior surface 14 is adapted to face toward a bone surface and is most typically implanted in contact with the adjacent bone. Interior surface 14 is substantially or entirely non-porous in order to prevent ingrowth of the adjacent hard tissue.

By "substantially or entirely non-porous" is meant that a substantial portion of the area of the particular surface, e.g., in excess of about 70% of the area of that surface, is either non-porous of has pores adequately small to prevent ingrowth of hard tissue to the extent that dissection of the implant from the hard tissue surface is difficult. Such a dissection would involve only the application of a slight amount of force or the very minimal use of a scalpel to free the implant from the adjacent bone.

While it is preferred that the convex surface is porous and the concave surface is non-porous, for purposes of the present invention it is only necessary that the opposing surface of the implant have different porosity characteristics in order that one surface allows for the ingrowth of soft tissue while the opposing surface substantially precludes the ingrowth of hard tissue.

Implant 10 is specifically a three dimensional shape suitable for the intended space filling application. As such it is of variable thickness between the opposing sides and is thus not planar in the fashion of a sheet or laminated sheets of material which have a substantially uniform thickness regardless of which point on the surface is chosen for a thickness determination.

Figure 2:
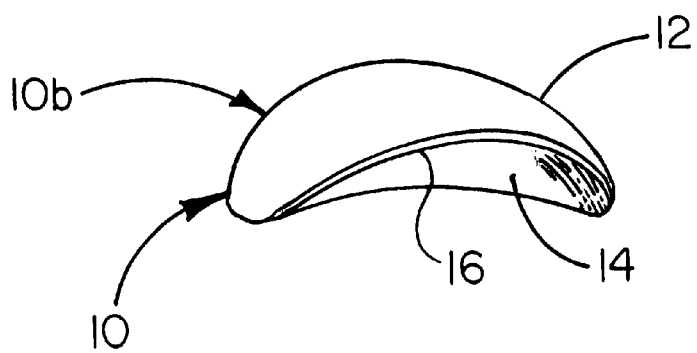
FIG. 2 is a perspective view of a typically shaped facial implant for cheek repairs, made according to the present invention.

FIG. 2 shows a perspective view of a facial implant 10 of the present invention suitably shaped for a typical cheek repair. The specific example shown is a malar or submalar implant and is intended as representative of cheek implants 10b of any type. Implant 10b, as with chin implant 10a, has a convex surface 12 opposing a concave surface 14. Again, the convex surface 12 is adapted for facing outwardly toward the covering skin and to be in contact with soft tissue, and as such is provided with porosity appropriate to accommodate ingrowth of the soft tissue. Concave surface 14 is alternatively non-porous or substantially non-porous in order to substantially preclude ingrowth of the adjacent hard tissue that the concave surface is adapted to face toward and substantially be in contact with.

Figure 3:
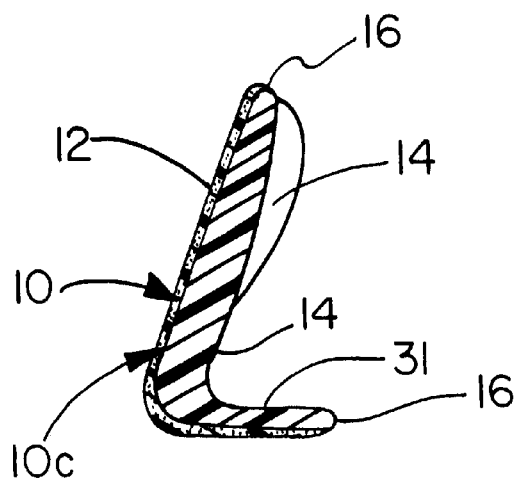
FIG. 3 is a cross sectional view of a typically shaped facial implant for nasal repairs, in this instance a nasal dorsal implant made according to the present invention.

FIG. 3 shows a cross sectional view of a typical nasal implant 10 of the present invention, in this instance a nasal dorsal implant 10c. Implants 10c of this type are described by, for example, U.S. Pat. No. 5,133,754 to Laghi. The implant shown is intended only to be representative of nasal implants generally, made as taught according to the present invention. For example, while FIG. 3 shows a nasal implant 10c having columella portion 31, it is well known in the art that many nasal dorsal implants do not include that portion.

While the various figures generally describe chin, cheek and nasal implants, these are intended to be representative of facial implants generally and the invention is not intended to be limited to only the types of implants described by the figures.

It is anticipated that implant devices according to the present invention will be sold with instructions for use describing that the porous surface is adapted for facing outwardly toward the skin and is intended to allow the ingrowth of the overlying soft tissue in contact with the porous surface of the implant. Likewise, such instructions would also describe that the non-porous or substantially non-porous implant surface is adapted for facing bone and intended to be implanted with that side substantially in contact with the hard tissue.

While one side of the inventive implant may be made porous by various known methods of inducing porosity into silicone materials, and thus allowing for the implant to be made entirely from silicone, it is preferred that the porous surface be made from ePTFE having a mean fibril length of about 8 microns or larger. Mean fibril lengths of about 10, 12, 14, 16, 18, 20, 22, 24, 26, 28, 30, 40, 50 or 60 microns or larger may also be used to allow ingrowth of soft tissue. A particularly preferred ePTFE is Gore S.A.M. non reinforced sheeting, p.n. 1SAM102, available W. L. Gore & Associates, Inc., Flagstaff, Ariz. This material has a mean fibril length of about 22 microns. Fibril length measurement is taught by U.S. Pat. No. 5,747,128 at col. 6, lines 19–37 and is considered to be a way of characterizing pore size for ePTFE materials.

A suitable implant may be fabricated by adhering a sheet of the ePTFE material to one surface, typically the convex surface, of a silicone space-filling implant. Typical of such implants are TEAC Terino Extended Anatomical™ Chin Implants and CSM Combined Submalar Shell™ both available in various sizes from Implantech Associates, Inc., 2064 Eastman Ave., #101, Ventura, Calif. These are both solid-core (i.e., non-hollow core) implants, being respectively silicone chin and cheek implants. The ePTFE is adhered to the desired surface using Nusil Silicone Type A MED 1137 adhesive (Nusil Technology, 1050 Cindy Ln., Carpinteria, Calif.), which is a biocompatible adhesive acceptable for implantation. The adhesive will penetrate into the void space of the adhesive-coated surface of the ePTFE sheet material. This interpenetration may be aided if desired by the use of a suitable silicone solvent to wet out the surface of the ePTFE prior to application of the adhesive ot that surface. Pressure may be applied to the ePTFE after that material has been applied to the silicone implant surface in order to ensure that the ePTFE is uniformly adhered to the silicone. This may be accomplished by a mold or clamping device of suitable shape. After allowing the adhesive to cure, the edges 16 (FIGS. 1–3) of the sheet of ePTFE are trimmed smoothly to match the edge of the surface of the silicone implant using appropriate sharp scissors or a scalpel blade.

While particular embodiments of the present invention have been illustrated and described herein, the present invention should not be limited to such illustrations and descriptions. It should be apparent that changes and modifications may be incorporated and embodied as part of the present invention within the scope of the appended claims.

We claim:

1. A facial space-filling implant comprising a three dimensional article having opposing convex and concave surfaces and a variable thickness therebetween, said thickness comprising a solid, non-hollow core, wherein said convex surface is substantially porous having void spaces of a size adequate to allow soft tissue ingrowth into a substantial portion of the void spaces, and wherein said concave surface is substantially non-porous to substantially preclude the ingrowth of hard tissue into the concave surface.

2. An implant according to claim 1 wherein said convex surface is adapted to face outwardly toward the skin of a patient and the convex surface is adapted to face toward a hard tissue surface of the patient.

3. An implant according to claim 2 wherein said thickness is adapted to be substantially orthogonal to the hard tissue.

4. An implant according to claim 2 wherein said convex surface comprises porous polytetrafluoroethylene.

5. An implant according to claim 2 wherein said core comprises an elastomer.

6. An implant according to claim 5 wherein said core comprises silicone.

7. An implant according to claim 5 wherein said core comprises polyurethane.

8. An implant according to claim 5 wherein said core comprises a fluoroelastomer.

\* \* \* \* \*